United States Patent [19]

Read et al.

[11] Patent Number: 4,563,768
[45] Date of Patent: Jan. 7, 1986

[54] MAMOGRAPHIC DEVICE USING LOCALIZED COMPRESSION CONE

[75] Inventors: Mark E. Read, Woodstock; Ronald L. Boswell, Charlottesville, both of Va.

[73] Assignee: University of Virginia Alumni Patents Foundations, Charlottesville, Va.

[21] Appl. No.: 512,870

[22] Filed: Jul. 11, 1983

[51] Int. Cl.⁴ .................. A61B 6/04; A61B 10/00; G03B 42/02; H05G 1/28
[52] U.S. Cl. .................. 378/037; 128/754; 378/164; 378/180
[58] Field of Search .......... 378/37, 163, 164, 180, 378/208; 128/754

[56] References Cited

U.S. PATENT DOCUMENTS

| | | | |
|---|---|---|---|
| 3,365,575 | 1/1968 | Strax | 378/37 |
| 3,547,121 | 12/1970 | Cherry . | |
| 4,048,507 | 9/1977 | Gaston . | |
| 4,090,084 | 5/1978 | Epstein et al. . | |
| 4,259,585 | 3/1981 | Novak et al. . | |

OTHER PUBLICATIONS

Muhlow, "A Device for Precision Needle Biopsy of the Breast at Mammograph," AJR 121: 843–845, 1974.

Primary Examiner—Alfred E. Smith
Assistant Examiner—T. N. Grigsby
Attorney, Agent, or Firm—John J. Byrne; Bradford E. Kile; Kevin M. O'Brien

[57] ABSTRACT

A mammographic device comprises an X-ray source for emitting X-rays along a predetermined path, a film holder disposed in the predetermined path of the X-rays for holding film to be exposed to the X-rays, a compression plate disposed in the predetermined path of the X-rays, and positionable for compressing, and holding in position, against the film holder a woman's breast to be X-rayed, and a suspension arrangement disposed between the X-ray source and the compression plate for holding the X-ray source and the compression plate in a fixed relative mutual position so that the distance between the X-ray source and the compression plate remains constant. In a preferred embodiment of the invention, the compression plate holder and compression plate are formed into an integral structure made of plexiglass. Preferably, the compression plate contains a matrix pattern of holes or perforations for facilitating biopsy guidance and needle aspiration cytology.

19 Claims, 4 Drawing Figures

MAMOGRAPHIC DEVICE USING LOCALIZED COMPRESSION CONE

DESCRIPTION

1. Technical Field

The present invention relates to a mammographic device using a localized compression cone, and specifically to a device in which the distance between an X-ray source and a compression plate is held fixed.

2. Background Art

Effective diagnostic techniques in the early detection and diagnosis of breast cancer include the utilization of mammographic devices in conjunction with needle biopsy. If, during the mammographic procedure, a non-palpable tumor is detected, it is often difficult to obtain a representative needle biopsy or to localize the tumor during surgical procedures. Nevertheless, a biopsy is of great importance, especially in cases involving small tumors, since early correct diagnosis means better prognosis.

In order to render needle biopsy more easily achievable in non-palpable tumors, various devices for precision needle biopsy of the breast during mammographic procedures have been developed. A typical device is disclosed by A. Muchlow in "A Device for Precision in Needle Biopsy of the Breast at Mammography", *AGR*, Vol. 121, pages 843–845 (1974).

In the latter article, there is described an apparatus which includes a film-holder table, on two opposite sides of which are placed profiled rails creating two slits, a lower slit holding a film, and another slit above the lower slit holding a plexiglass screen upon which the breast is positioned during the mammographic procedure. In that arrangement, vertical iron rods serve as guides for a compression plate, made of duraluminum, the compression plate holding a plexiglass window having perforations therein. The perforations or holes are marked in a coordinate system, and the compression plate can be locked in place at variable distances from the table by a locking mechanism. In this arrangement, when a breast has been compressed between the plexiglass screen and the compression plate for purposes of mammography, the film (once exposed) can be withdrawn from its slit while the breast remains positioned in a stationary manner.

Other mammographic compression devices are disclosed in U.S. Pat. No. 4,090,084—Epstein et al and U.S. Pat. No. 4,259,585—Novak et al.

Further arrangements are disclosed in the following U.S. Pat. Nos.: 3,577,160—White; 3,578,971—Lasky; 3,824,397—Bauer et al; 3,971,950—Evans et al; 3,991,316—Schmidt et al; and 4,097,748—Monvoisin.

Finally, various radiographic attachments and techniques are disclosed in the following U.S. Pat. Nos.: 3,111,582—Levi; 3,508,552—Hainault; 3,547,121—Cherry; 3,711,712—McLaren; 3,836,776—Gullekson; 3,913,561—Maeda; 3,848,136—Seldin; 4,048,507—de Gaston; 4,061,924—Jacoby et al; 4,163,900—Warren et al; and 4,181,859—Vitalini.

Such devices and attachments of the prior art have various disadvantages. Principal among these disadvantages is that of poor reproduction as a result of poor focussing of the X-ray tube with respect to the object being X-rayed. In mammographic devices such as the one disclosed in the aforementioned article, such poor focussing and low quality reproduction are a direct result of the fact that the distance between the X-ray tube and the object being X-rayed is not fixed.

The latter characteristic can also lead to unacceptable variation in the intensity of the X-rays being emitted by the tube, and this leads to the development of a picture which is not as "clean" as it should be. Moreover, a further disadvantage resulting from lack of a fixed distance between the X-ray tube and the object being X-rayed is lack of maintenance of alignment between the X-ray tube and the compression plate, specifically between the X-ray tube and the holes or perforations in the compression plate.

DISCLOSURE OF INVENTION

The present invention relates to a mammographic device using a localized compression cone, and more specifically to a mammographic device in which an X-ray source and a compression plate are held in a fixed relative mutual position so that the distance between the X-ray source and the compression plate remains constant.

A preferred embodiment of the mammographic device of the present invention comprises an X-ray source for emitting X-rays along a predetermined path, a film holder disposed in the predetermined path of the X-rays for holding film to be exposed thereto, a compression plate disposed in the predetermined path of the X-rays and positionable for compressing, and holding in position, against the film holder a breast to be X-rayed, and a suspension arrangement for holding the X-ray source and the compression plate in a fixed relative mutual position so that the distance therebetween remains constant.

As previously stated, the maintenance of a fixed distance between the X-ray tube and the object being X-rayed results in better focussing of the X-ray beam with respect to the object being X-rayed, better picture reproduction, better alignment between the X-ray tube and the compression plate (including the perforations or holes contained therein), and non-variation in the intensity of the X-rays from one patient to the next.

The preferred embodiment of the invention further includes a compression plate which has perforations or holes arranged in a predetermined pattern or matrix therein. As will be seen in the detailed description below, this facilitates biopsy guidance and needle aspiration cytology.

Therefore, it is a primary object of the present invention to provide a mammographic device using a localized compression cone.

It is a further object of the present invention to provide a mammographic device wherein a fixed relative mutual position is maintained between an X-ray source and a compression plate so that the distance therebetween remains constant.

It is a further object of the present invention to provide a mammographic device having a compression plate which contains a matrix or pattern of holes or perforations to facilitate biopsy guidance and needle aspiration cytology.

The manner in which these and other objects of the present invention are accomplished will become clear from the following detailed description of a preferred embodiment.

BEST MODE FOR CARRYING OUT THE INVENTION

The best mode for carrying out the invention will now be described with reference to various figures of the drawings.

Figure 1:
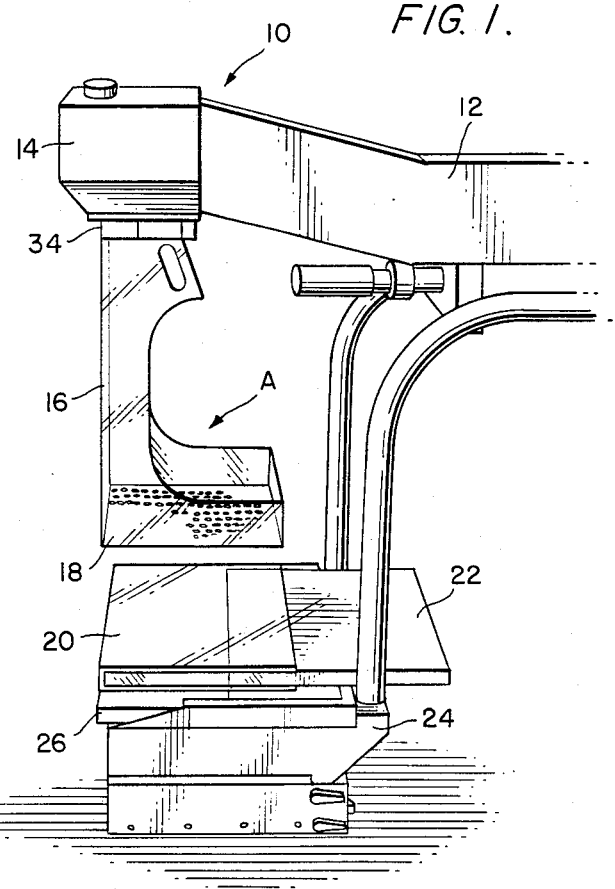
FIG. 1 is a perspective view of the mammographic device of the present invention.

FIG. 1 is a perspective view of the mammographic device of the present invention. As seen therein, the device 10 comprises an X-ray support 12, an X-ray source 14, a compression plate holder 16, a compression plate 18, film holder 20, and base 24.

Figure 2:
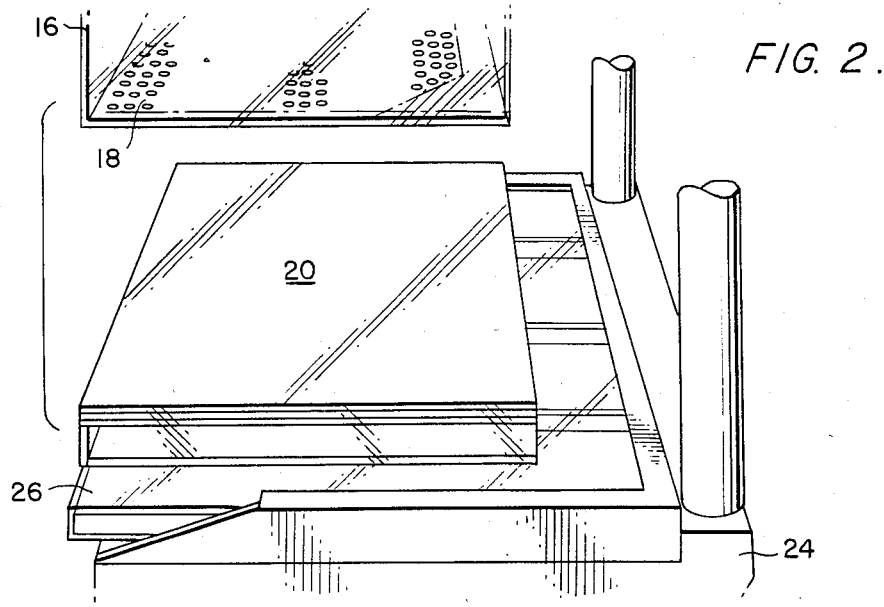
FIG. 2 is a perspective view of the film holder of the device of the present invention.

FIG. 2 is a perspective view of the film holder 20 of FIG. 1, the film holder 20 being positioned on a flat structure 26, which is itself positioned on the base 24.

Figure 4:
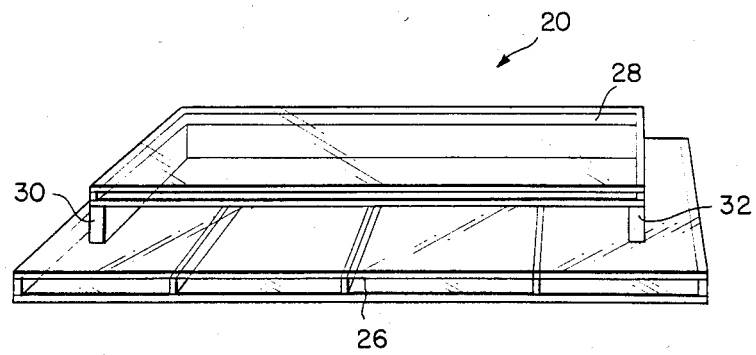
FIG. 4 is a rear view of the film holder of FIG. 1.

FIG. 4 is a rear view of the film holder 20, as positioned on the supporting structure 26. As seen therein, the film holder 20 comprises a sheet of plexiglass material 28, supported by side supporting members 30 and 32 which provide elevation of the plexiglass sheet 28 with respect to the lower supporting structure 26. As a result, the film 22 (FIG. 1) is easily slipped into the space underlying the plexiglass sheet 28 and located between the side supporting members 30 and 32.

Figure 3:
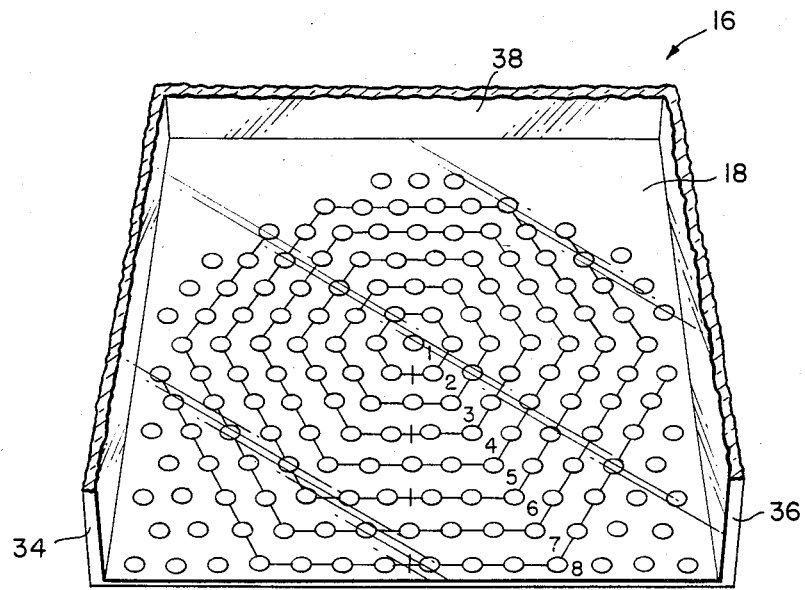
FIG. 3 is a perspective view of the compression plate holder and compression plate, taken along arrow A in FIG. 1.

FIG. 3 is a perspective view of the compression plate 18, as supported by the compression plate holder 16, and as seen by viewing along the arrow A of FIG. 1. The compression plate holder 16 is seen to include sidewalls 34 and 36, and rear wall 38, the latter walls providing a suspended connection between the X-ray source 14 and the compression plate 18, thus maintaining a fixed distance between the source 14 and the compression plate 18.

The compression plate 18 is seen to contain a matrix or pattern of holes or perforations, arranged in concentric sexagonal arrays or rings, each array or ring being labelled by a respective identifying number 1, 2, . . . , 7, 8. Preferably, the compression plate holder 16 and the compression plate 18 are formed into a single integral structure, and are made of plexiglass.

The compression plate holder 16 and the compression plate 18 together form a suspended structure including a laterally arctuated recess for facilitating operator manipulation in the space directly above the compression plate 18.

Returning to consideration of FIG. 1, it is to be noted that the compression plate holder 16 which supports compression plate 18 is connected to the X-ray source 14 by a connector or joint 34, so that the X-ray source 14, the compression plate holder 16 and the compression plate 18 form a contiguous structure and are maintained in a fixed positional relationship relative to each other. As a result, the distance between the X-ray source 14 and the compression plate 18 remains fixed at all times, regardless of the particular patient being X-rayed.

Operation of the mammographic device of the present invention is as follows. With reference to FIG. 1, the patient to be X-rayed stands to the left of the structure in FIG. 1, and the breast to be X-rayed is placed on the upper surface of film holder 20, while the X-ray source 14, compression plate holder 16 and compression plate 18 are lowered so that the breast to be X-rayed is compressed between the compression plate 18 and the upper surface of the film holder 20.

Film 22 is inserted into film holder 20, and an X-ray is taken. While the X-ray is being developed, the patient remains in a stationary position with respect to the mammographic device 10, so that the positioning of the breast with respect to the X-ray source 14 is not disturbed. Once the X-ray is developed, the physician examines the X-ray to locate any lesions.

If a lesion is found, a local anesthetic is administered to the patient, and then, in accordance with the known procedure (as described in the aforementioned article cited above), a needle is inserted into the lesion. With reference to FIG. 3, this procedure is facilitated by use of the labeled holes 1–8 in compression plate 18, as such holes 1–8 appear on the X-ray examined by the physician. That is to say, the physician uses the holes 1–8 on compression plate 18, as they appear on the X-ray, to accurately locate the lesion, and then uses the holes 1–8 on the compression plate 18 itself as a guide during insertion of the needle.

Once the needle is inserted, the compression plate 18 is lifted from the patient, and the patient can then be released for immediate accomplishment of the biopsy procedure.

A primary feature of the invention resides in the fact that, as a result of the connection of the X-ray source 14, the compression plate holder 16 and the compression plate 18 into a single, integral structure, a fixed distance is maintained between the X-ray source 14 and the compression plate 18, and thus between the X-ray source 14 and the object being X-rayed. The resulting advantage of this feature is better focussing of the X-ray source and X-ray beam with respect to the object being X-rayed, and this results in a better X-ray picture reproduction.

In addition, by virtue of the specific arrangement of the present invention, alignment is maintained between the X-ray source 14 and the compression plate 18, including the holes 1–8 contained therein.

Furthermore, the specific arrangement of the present invention results in non-variation in the intensity of X-rays emitted by the source 14, and this also results in a "cleaner" X-ray picture.

Use of the matrix of holes in the compression plate 18 (see FIG. 3) also produces several advantages. Use of the holes 1–8 in the compression plate 18 results in more consistent and precise localization of any lesion detected. In addition, there is less risk of complication (for example, due to infection) by virtue of the fact that multiple needle insertions are avoided by use of the matrix of holes 1–8 in the compression plate 18.

The increased accuracy and consistency in localizing the lesion also results in a decreased need for retaking the X-rays, with resultant lessened radiation exposure of the patient.

The increased accuracy in localizing the lesion, by use of the perforated compression plate 18, makes it possible for the surgeon to remove only a minimal amount of tissue for the purpose of pathological analysis. This results in less discomfort to the patient and quicker pathological examination of the tissue by the pathologist.

Finally, the present invention results in consumption of less operating room time, and resultant reduced expense in health care.

While a preferred form and arrangement of the present invention has been illustrated in this application, it is to be understood that various modifications and changes in the arrangement may be made without departing from the spirit and scope of this disclosure.

We claim:

1. A Mammographic device comprising:
   X-ray source means for emitting X-rays along a predetermined path;
   film holder means disposed in the predetermined path of the X-rays for holding film to be exposed to the X-rays;
   compression plate means disposed in the predetermined path of the X-rays, and positionable for compressing, and holding in position, against the film holder means a woman's breast to be X-rayed; and
   suspension means suspended between the X-ray source means and the compression plate means for holding the X-ray source means and the compression plate means in a fixed relative mutual position so that the distance between the X-ray source means and the compression plate means remains constant;
   said compression plate means and said suspension means together forming a suspended structure having a laterally arctuated recess permitting operator manipulation therein.

2. The device of claim 1, wherein said suspension means comprises a compression plate holder.

3. The device of claim 2, wherein said compression plate holder is made of plexiglass.

4. The device of claim 2, wherein said X-ray source means is positioned vertically above said film holder means, said compression plate holder comprising a structure extending vertically downward from said X-ray source means.

5. The device of claim 4, wherein said structure extending vertically downward from said X-ray source means comprises two vertically disposed flat sidewalls extending vertically downward from said X-ray source means, said compression plate means comprising a compression plate horizontally situated between remote ends of said two vertically disposed flat sidewalls.

6. The device of claim 5, wherein said two vertically disposed flat sidewalls and said compression plate are formed into an integral structure.

7. The device of claim 6, wherein said integral structure is made of plexiglass.

8. The device of claim 5, wherein said compression plate is perforated with holes arranged in a predetermined matrix.

9. The device of claim 5, wherein said two vertically disposed flat sidewalls and said compression plate are made of plexiglass.

10. The device of claim 4, wherein said structure extending vertically downward from said X-ray source means is made of plexiglass.

11. The device of claim 4, wherein said compression plate means comprises a compression plate horizontally situated and held in position by said compression plate holder at an end thereof remote from said X-ray source means.

12. The device of claim 11, wherein said compression plate is perforated with holes arranged in a predetermined matrix.

13. A device as recited in claim 1, wherein said compression plate means comprises a compression plate located in a generally transverse direction to said predetermined path; said compression plate having perforated holes thereon arranged in a predetermined matrix.

14. A mammographic device comprising:
   X-ray source means for emitting X-rays along a predetermined path;
   film holder means disposed in the predetermined path of the X-rays for holding film to be exposed to the X-rays;
   compression plate means disposed in the predetermined path of the X-rays, and positionable for compressing, and holding in position, against the film holder means a woman's breast to be X-rayed; and
   suspension means suspended between the X-ray source means and the compression plate means for holding the X-ray source means and the compression plate means in a fixed relative mutual position so that the distance between the X-ray source means and the compression plate means remains constant;
   said suspension means comprises a compression plate holder;
   said compression plate holder is made of plexiglass.

15. A Mammographic device comprising:
   X-ray source means for emitting X-rays along a predetermined path;
   film holder means disposed in the predetermined path of the X-rays for holding film to be exposed to the X-rays;
   compression plate means disposed in the predetermined path of the X-rays, and positionable for compressing, and holding in position, against the film holder means a woman's breast to be X-rayed; and
   suspension means suspended between the X-ray source means and the compression plate means for holding the X-ray source means and the compression plate means in a fixed relative mutual position so that the distance between the X-ray source means and the compression plate means remains constant;
   said suspension means comprises a compression plate holder;
   said X-ray source means is positioned vertically above said film holder means, said compression plate holder comprising a structure extending vertically downward from said X-ray source means;
   said structure extending vertically downward from said X-ray source means comprises two vertically disposed flat sidewalls extending vertically downward from said X-ray source means, said compression plate means comprising a compression plate horizontally situated between remote ends of said two vertically disposed flat sidewalls;
   said two vertically disposed flat sidewalls and said compression plate are formed into an integral structure;
   said integral structure is made of plexiglass.

16. A Mammographic device comprising:
   X-ray source means for emitting X-rays along a predetermined path;
   film holder means disposed in the predetermined path of the X-rays for holding film to be exposed to the X-rays;
   compression plate means disposed in the predetermined path of the X-rays, and positionable for compressing, and holding in position, against the film holder means a woman's breast to be X-rayed; and suspension means suspended between the X-ray source means and the compression plate means for holding the X-ray source means and the compression plate means in a fixed relative mutual position so that the distance between the X-ray source means and the compression plate means remains constant;

said suspension means comprises a compression plate holder;

said X-ray source means is positioned vertically above said film holder means, said compression plate holder comprising a structure extending vertically downward from said X-ray source means;

said structure extending vertically downward from said X-ray source means comprises two vertically disposed flat sidewalls extending vertically downward from said X-ray source means, said compression plate means comprising a compression plate horizontally situated between remote ends of said two vertically disposed flat sidewalls;

said compression plate is perforated with holes arranged in a predetermined matrix.

17. A Mammographic device comprising:

X-ray source means for emitting X-rays along a predetermined path;

film holder means disposed in the predetermined path of the X-rays for holding film to be exposed to the X-rays;

compression plate means disposed in the predetermined path of the X-rays, and positionable for compressing, and holding in position, against the film holder means a woman's breast to be X-rayed; and suspension means suspended between the X-ray source means and the compression plate means for holding the X-ray source means and the compression plate means in a fixed relative mutual position so that the distance between the X-ray source means and the compression plate means remains constant;

said suspension means comprises a compression plate holder;

said X-ray source means is positioned vertically above said film holder means, said compression plate holder comprising a structure extending vertically downward from said X-ray source means;

said structure extending vertically downward from said X-ray source means comprises two vertically disposed flat sidewalls extending vertically downward from said X-ray source means, said compression plate means comprising a compression plate horizontally situated between remote ends of said two vertically disposed flat sidewalls;

said two vertically disposed flat sidewalls and said compression plate are made of plexiglass.

18. A Mammographic device comprising:

X-ray source means for emitting X-rays along a predetermined path;

film holder means disposed in the predetermined path of the X-rays for holding film to be exposed to the X-rays;

compression plate means disposed in the predetermined path of the X-rays, and positionable for compressing, and holding in position, against the film holder means a woman's breast to be X-rayed; and suspension means suspended between the X-ray source means and the compression plate means for holding the X-ray source means and the compression plate means in a fixed relative mutual position so that the distance between the X-ray source means and the compression plate means remains constant;

said suspension means comprises a compression plate holder;

said X-ray source means is positioned vertically above said film holder means, said compression plate holder comprising a structure extending vertically downward from said X-ray source means;

said structure extending vertically downward from said X-ray source means is made of plexiglass.

19. A Mammographic device comprising:

X-ray source means for emitting X-rays along a predetermined path;

film holder means disposed in the predetermined path of the X-rays for holding film to be exposed to the X-rays;

compression plate means disposed in the predetermined path of the X-rays, and positionable for compressing, and holding in position, against the film holder means a woman's breast to be X-rayed; and suspension means suspended between the X-ray source means and the compression plate means for holding the X-ray source means and the compression plate means in a fixed relative mutual position so that the distance between the X-ray source means and the compression plate means remains constant;

said suspension means comprises a compression plate holder;

said X-ray source means is positioned vertically above said film holder means, said compression plate holder comprising a structure extending vertically downward from said X-ray source means;

said compression plate means comprises a compression plate horizontally situated and held in position by said compression plate holder at an end thereof remote from said X-ray source means;

said compression plate is perforated with holes arranged in a predetermined matrix.

* * * * *